(12) United States Patent
Wildes et al.

(10) Patent No.: US 7,105,986 B2
(45) Date of Patent: Sep. 12, 2006

(54) ULTRASOUND TRANSDUCER WITH ENHANCED THERMAL CONDUCTIVITY

(75) Inventors: Douglas Glenn Wildes, Ballston Lake, NY (US); Charles Edward Baumgartner, Niskayuna, NY (US); Petrus Joannes Joseph Moeleker, Latham, NY (US); Bruno Hans Haider, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 4 days.

(21) Appl. No.: 10/929,019

(22) Filed: Aug. 27, 2004

(65) Prior Publication Data

US 2006/0043839 A1   Mar. 2, 2006

(51) Int. Cl.
*H01L 41/08* (2006.01)
(52) U.S. Cl. .................. 310/327; 310/334; 310/346
(58) Field of Classification Search ............... 310/326, 310/327, 334–337
See application file for complete search history.

(56) References Cited

U.S. PATENT DOCUMENTS

| 4,751,420 | A | * | 6/1988 | Gebhardt et al. | 310/327 |
| 5,267,221 | A | | 11/1993 | Miller et al. | 367/140 |
| 5,329,498 | A | | 7/1994 | Greenstein | 367/155 |
| 5,545,942 | A | * | 8/1996 | Jaster et al. | 310/341 |
| 5,560,362 | A | | 10/1996 | Sliwa, Jr. et al. | 128/660.03 |
| 5,629,906 | A | * | 5/1997 | Sudol et al. | 367/162 |
| 5,648,942 | A | * | 7/1997 | Kunkel, III | 367/176 |
| 5,721,463 | A | * | 2/1998 | Snyder | 310/334 |
| 6,467,138 | B1 | * | 10/2002 | Aime | 29/25.35 |

* cited by examiner

*Primary Examiner*—Mark Budd
(74) *Attorney, Agent, or Firm*—Fletcher Yoder

(57) ABSTRACT

A composite structure of a backing material with enhanced conductivity for use in a transducer is presented. The composite structure includes a plurality of layers of backing material alternatingly arranged with a plurality of thermal conductive elements, wherein the plurality of thermal conductive elements are configured to transfer heat from a center of the transducer to a plurality of points on the composite structure of backing material.

97 Claims, 4 Drawing Sheets

ULTRASOUND TRANSDUCER WITH ENHANCED THERMAL CONDUCTIVITY

BACKGROUND

The invention relates generally to transducers, and more specifically to transducers with increased thermal conductivity.

Transducers, such as acoustic transducers, have found application in medical imaging wherein an acoustic probe is held against a patient and the probe transmits and receives ultrasound waves, which in turn may facilitate the imaging of the internal tissues of the patient. It may be advantageous to operate the acoustic probe at a maximum permissible acoustic intensity to enable higher quality imaging, which may be achieved via better penetration of the acoustic waves into the patient's tissues. However, operating the acoustic probe at higher acoustic intensities may disadvantageously result in the production of excessive heat in the transducer assembly.

Moreover, there exist limits on the maximum external temperature of an acoustic probe at points of contact with the patient and a technician. Furthermore, in certain modes of operation of the acoustic probe, the heat generated within the transducer elements or within the transducer assembly may cause the temperature of some regions of the probe surface to exceed permissible limits. However, as will be appreciated by one skilled in the art, materials typically employed to fabricate the transducer elements are primarily selected based upon their acoustic properties, and are generally known to possess relatively low thermal conductivity. Furthermore, the transducer elements are generally isolated from one another by dicing kerfs that provide additional thermal insulation of the transducer elements. Hence, the heat generated within the transducer elements is trapped in the acoustic stack causing the face temperature of the probe to rise above the ambient temperature. It may be advantageous to dissipate the heat that may be trapped in the array of transducer elements in order to circumvent the overheating of the patient contact surfaces of the transducer assembly.

Transducer assemblies are generally fabricated employing materials with lower intrinsic thermal conductivity. The low thermal conductivity of transducer assemblies may result in the overheating of the probe. Disadvantageously, many previous attempts to enhance the thermal conductivity of the acoustic probe have had limited effect on the face temperature of the probe and therefore may be ineffective in sufficiently reducing the face temperature enough to prevent discomfort to a patient. Other prior techniques have been more successful at sufficiently reducing face temperature of the probe, but this improvement often comes at the expense of the acoustic performance of the transducer assembly.

It would be desirable draw the heat away from the heat-generating region of the transducer assembly to lower the face temperature of the ultrasound probe to an acceptable level. Further, it would be desirable to lower the face temperature of the probe to facilitate the operation of the probe at a higher transmit power thereby yielding improvements in diagnostic imaging.

BRIEF DESCRIPTION

Briefly, in accordance with an exemplary embodiment of the present technique, a composite structure of a backing material for use in a transducer is presented. The composite structure includes a plurality of layers of backing material alternatingly arranged between a plurality of thermal conductive elements, wherein the plurality of thermal conductive elements are configured to transfer heat from a center of the transducer to a plurality of points on the composite structure of backing material.

According to a further embodiment of the present technique, a transducer assembly including a composite structure of backing material is presented. The transducer assembly includes a plurality of transducer elements disposed in a first layer having a first front face and a first rear face. Furthermore, the composite structure includes an absorber disposed in a second layer having a second front face and a second rear face, wherein the absorber is disposed adjacent to the first rear face, and is acoustically coupled to the first rear face, and wherein the absorber includes a composite structure of backing material having conductive elements dispersed therethrough.

In accordance with another embodiment of the present technique, a method for forming a composite structure of backing material for use in a transducer assembly is presented. The method includes dicing a block of backing material to form a plurality of layers of backing material. Furthermore, the method includes alternatingly disposing the plurality of layers of backing material between a plurality of thermal conductive elements to form the composite structure of backing material.

According to a further aspect of the present technique, an alternate method for forming a composite structure of backing material for use in a transducer assembly is presented. The method includes arranging a plurality of thermal conductive elements in a spaced relationship in a mold. Additionally, the method includes casting an absorber material around the plurality of thermal conductive elements to form the composite structure of backing material.

In accordance with a further aspect of the present technique, a method of manufacturing a transducer assembly is presented. The method includes disposing a plurality of acoustic transducer elements in a first layer having a first front face and a first rear face. Furthermore, the method includes providing a backing comprising an absorber disposed in a second layer having a second front face and a second rear face, wherein the absorber is disposed adjacent to the first rear face and is acoustically coupled to the first rear face, and wherein the absorber includes a composite structure of backing material having conductive elements dispersed therethrough.

According to yet another aspect of the present technique, an ultrasound system including a composite structure of backing material is presented. The system includes an acquisition subsystem configured to acquire ultrasound data, wherein the acquisition subsystem includes at least one transducer assembly, wherein the transducer assembly includes a composite structure of backing material having conductive elements dispersed therethrough. Additionally, the system includes a processing subsystem configured to process the ultrasound data acquired via the acquisition subsystem.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In many fields, such as medical imaging, transducer materials chosen for their acoustic properties typically possess lower thermal conductivity. Additionally, the individual transducer elements are often separated from one another by dicing kerfs that provide additional thermal insulation. Therefore, heat generated within the transducer assembly may be trapped within the transducer assembly thereby causing the face temperature of the transducer assembly to increase above permissible limits. It may be desirable to enhance the thermal conductivity of the transducer assembly, while maintaining the acoustic properties of the transducer assembly. The techniques discussed herein address some or all of these issues.

Figure 1:
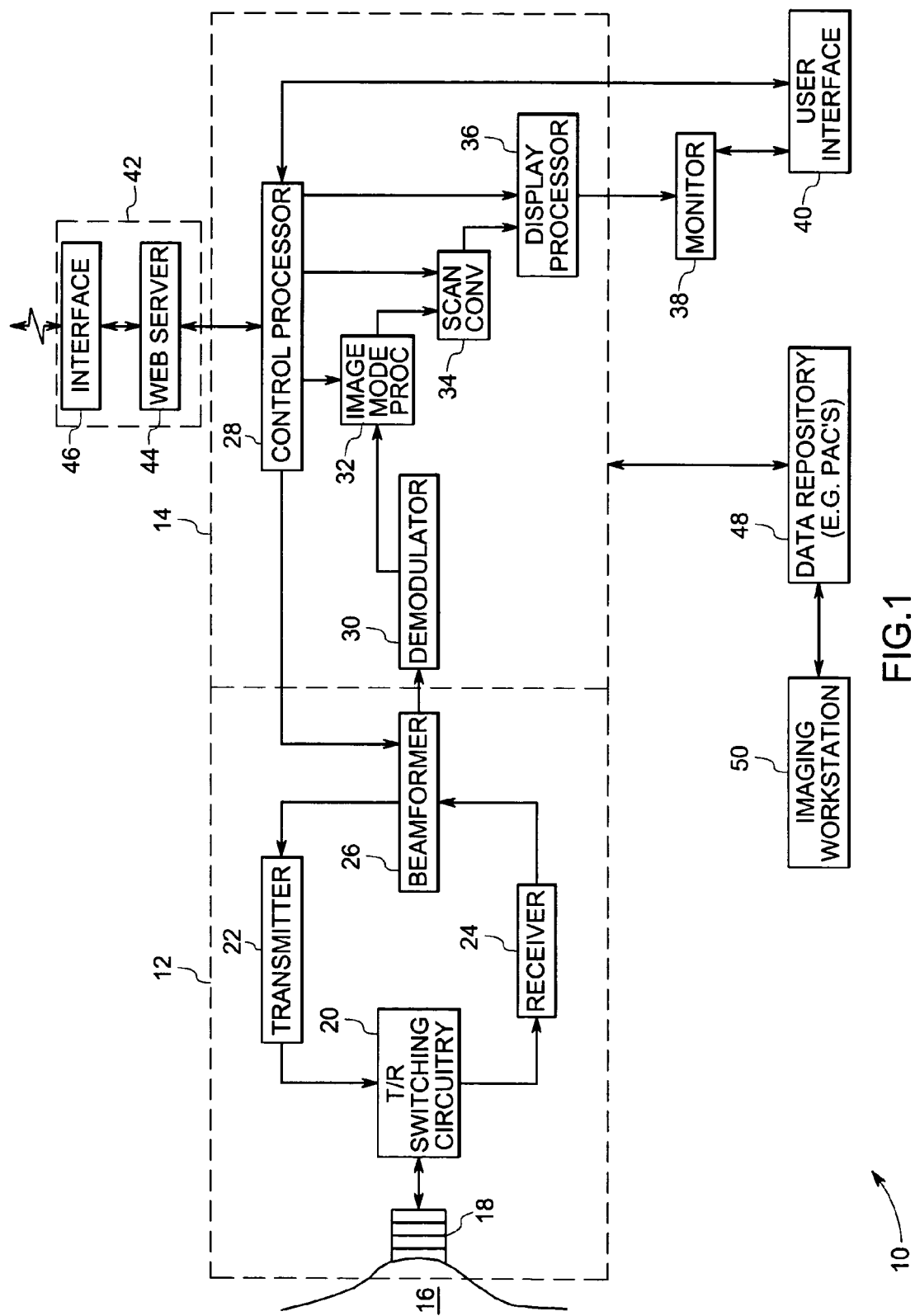
FIG. 1 is a diagrammatic illustration of an ultrasound system.

FIG. 1 is a block diagram of an embodiment of an ultrasound system 10. The ultrasound system includes an acquisition subsystem 12 and a processing subsystem 14. The acquisition subsystem 12 includes a transducer array 18 (having a plurality of transducer array elements), transmit/receive switching circuitry 20, a transmitter 22, a receiver 24, and a beamformer 26. The processing subsystem 14 includes a control processor 28, a demodulator 30, an imaging mode processor 32, a scan converter 34 and a display processor 36. The display processor 36 is further coupled to a display monitor 38 for displaying images. User interface 40 interacts with the control processor 28 and the display monitor 38. The control processor 28 may also be coupled to a remote connectivity subsystem 42 including a web server 44 and a remote connectivity interface 46. The processing subsystem 14 may be further coupled to a data repository 48 configured to receive ultrasound image data. The data repository 48 interacts with image workstation 50.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present ultrasound system 10 is provided by way of example, and the present techniques are in no way limited by the specific system configuration.

In the acquisition subsystem 12, the transducer array 18 is in contact with a patient or subject 16. The transducer array is coupled to the transmit/receive (T/R) switching circuitry 20. The T/R switching circuitry 20 is coupled to the output of transmitter 22 and the input of the receiver 24. The output of the receiver 24 is an input to the beamformer 26. The beamformer 26 is further coupled to the input of the transmitter 22 and to the input of the demodulator 30. The beamformer 26 is also coupled to the control processor 28 as shown in FIG. 1.

In the processing subsystem 14, the output of demodulator 30 is coupled to an input of an imaging mode processor 32. The control processor 28 interfaces with the imaging mode processor 32, the scan converter 34 and the display processor 36. An output of imaging mode processor 32 is coupled to an input of scan converter 34. An output of the scan converter 34 is coupled to an input of the display processor 36. The output of display processor 36 is coupled to the monitor 38.

The ultrasound system 10 transmits ultrasound energy into the subject 16 and receives and processes backscattered ultrasound signals from the subject 16 to create and display an image. To generate a transmitted beam of ultrasound energy, the control processor 28 sends command data to the beamformer 26 to generate transmit parameters to create a beam of a desired shape originating from a certain point at the surface of the transducer array 18 at a desired steering angle. The transmit parameters are sent from the beamformer 26 to the transmitter 22. The transmitter 22 uses the transmit parameters to properly encode transmit signals to be sent to the transducer array 18 through the T/R switching circuitry 20. The transmit signals are set at certain levels and phases with respect to each other and are provided to individual transducer elements of the transducer array 18. The transmit signals excite the transducer elements to emit ultrasound waves with the same phase and level relationships. As a result, a transmitted beam of ultrasound energy is formed in a subject 16 within a scan plane along a scan line when the transducer array 18 is acoustically coupled to the subject 16 by using, for example, ultrasound gel. The process is known as electronic scanning.

The transducer array 18 is a two-way transducer. When ultrasound waves are transmitted into a subject 16, the ultrasound waves are backscattered off the tissue and blood samples within the subject 16. The transducer array 18 receives the backscattered waves at different times, depending on the distance into the tissue they return from and the angle with respect to the surface of the transducer array 18 at which they return. The transducer elements convert the ultrasound energy from the backscattered waves into electrical signals.

The electrical signals are then routed through the T/R switching circuitry 20 to the receiver 24. The receiver 24 amplifies and digitizes the received signals and provides other functions such as gain compensation. The digitized received signals corresponding to the backscattered waves received by each transducer element at various times preserve the amplitude and phase information of the backscattered waves.

The digitized signals are sent to the beamformer 26. The control processor 28 sends command data to beamformer 26. The beamformer 26 uses the command data to form a receive beam originating from a point on the surface of the transducer array 18 at a steering angle typically corresponding to the point and steering angle of the previous ultrasound beam transmitted along a scan line. The beamformer 26 operates on the appropriate received signals by performing time delaying and focusing, according to the instructions of the command data from the control processor 28, to create received beam signals corresponding to sample volumes along a scan line in the scan plane within the subject 16. The phase, amplitude, and timing information of the received signals from the various transducer elements is used to create the received beam signals.

The received beam signals are sent to the processing subsystem 14. The demodulator 30 demodulates the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to the imaging mode processor 32. The imaging mode processor 32 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 34. The scan converter 34 processes the parameter data by performing a translation from scan sequence format to display format. The translation includes performing interpolation operations on the parameter data to create display pixel data in the display format.

The scan converted pixel data is sent to the display processor 36 to perform any final spatial or temporal filtering of the scan converted pixel data, to apply grayscale or color to the scan converted pixel data, and to convert the digital pixel data to analog data for display on the monitor 38. The user interface 40 is coupled to the control processor 28 to allow a user to interface with the ultrasound system 10 based on the data displayed on the monitor 38.

Figure 2:
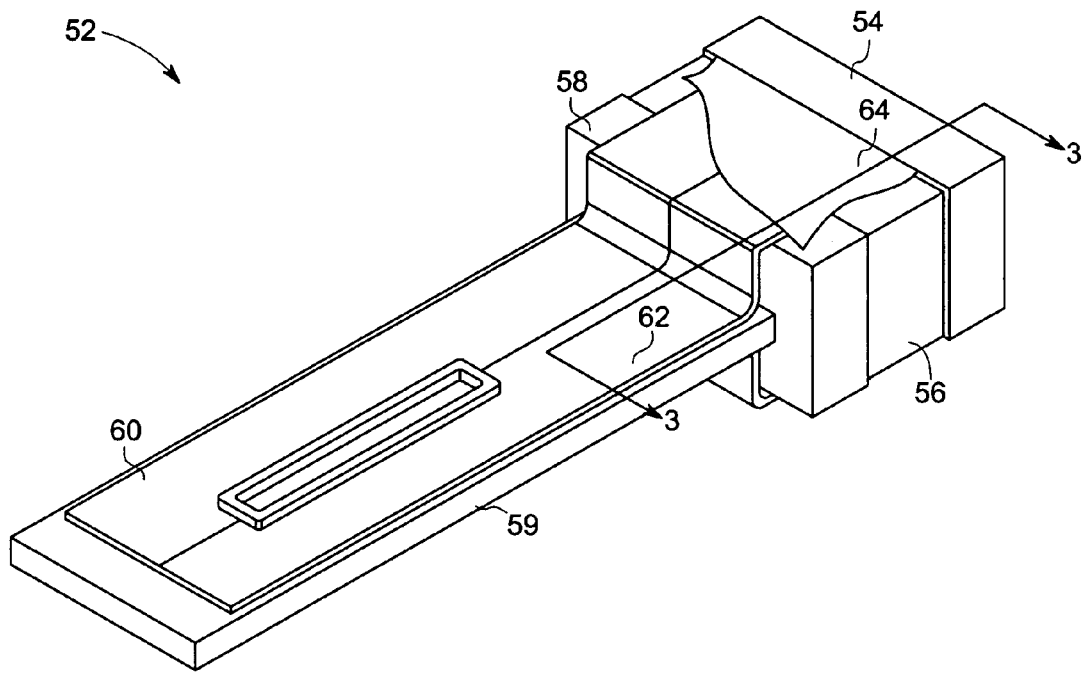
FIG. 2 is a perspective view of a transducer assembly.

FIG. 2 illustrates a perspective side view of a transducer assembly 52. Typically, the transducer assembly 52, for example, an acoustic transducer assembly, as illustrated in FIG. 2, may include one or more transducer elements (not shown), one or more matching layers (not shown) and a lens 54. The transducer elements may be arranged in a spaced relationship, such as, but not limited to, an array of transducer elements disposed on a layer, wherein each of the transducer elements may include a transducer front face and a transducer rear face. As will be appreciated by one skilled in the art, the transducer elements may be fabricated employing materials, such as, but not limited to lead zirconate titanate (PZT), polyvinylidene difluoride (PVDF) and composite PZT. The transducer assembly 52 may also include one or more matching layers disposed adjacent to the front face of the array of transducer elements, wherein each of the matching layers may include a matching layer front face and a matching layer rear face. The matching layers facilitate the matching of an impedance differential that may exist between the high impedance transducer elements and a low impedance patient or subject 16 (see FIG. 1). The lens 54 may be disposed adjacent to the matching layer front face and provides an interface between the patient and the matching layer.

Additionally, the transducer assembly 52 may include a backing layer 56, having a front face and a rear face, that may be fabricated employing a suitable acoustic damping material possessing high acoustic losses. The backing layer 56 may be acoustically coupled to the rear face of the array of transducer elements, wherein the backing layer 56 facilitates the attenuation of acoustic energy that may emerge from the rear face of the array of transducer elements.

Furthermore, the transducer assembly 52 may also include a support plate 58 configured to provide support to the transducer assembly 52 including the lens 54, the matching layers and the backing layer 56. The support plate 58 may include a T-shaped support plate, as illustrated in FIG. 2. Also, the support plate 58 may be coupled to the rear face of the backing layer 56. As will be appreciated by one skilled in the art, the support plate 58 may be fabricated employing metals such as, but not limited to, aluminum. Furthermore, a central plate 59 may be coupled to the support plate 58. The central plate 59 may facilitate the dissipation of heat as will be described hereinafter. Circuitry 60, such as flexible printed circuits, that may for example include copper signal and ground conductors on a polyimide substrate, may be disposed on the central plate 59. Additionally, as illustrated in FIG. 2, a split ground plane 62 facilitates the separation of the transmitting and receiving regions of the transducer assembly 52.

Moreover, the transducer assembly 52 may also include an electrical shield 64 that facilitates the isolation of the transducer elements from the external environment. The electrical shield may include metal foils, wherein the metal foils may be fabricated employing metals such as, but not limited to, copper, aluminum, brass, and gold.

Figure 3:
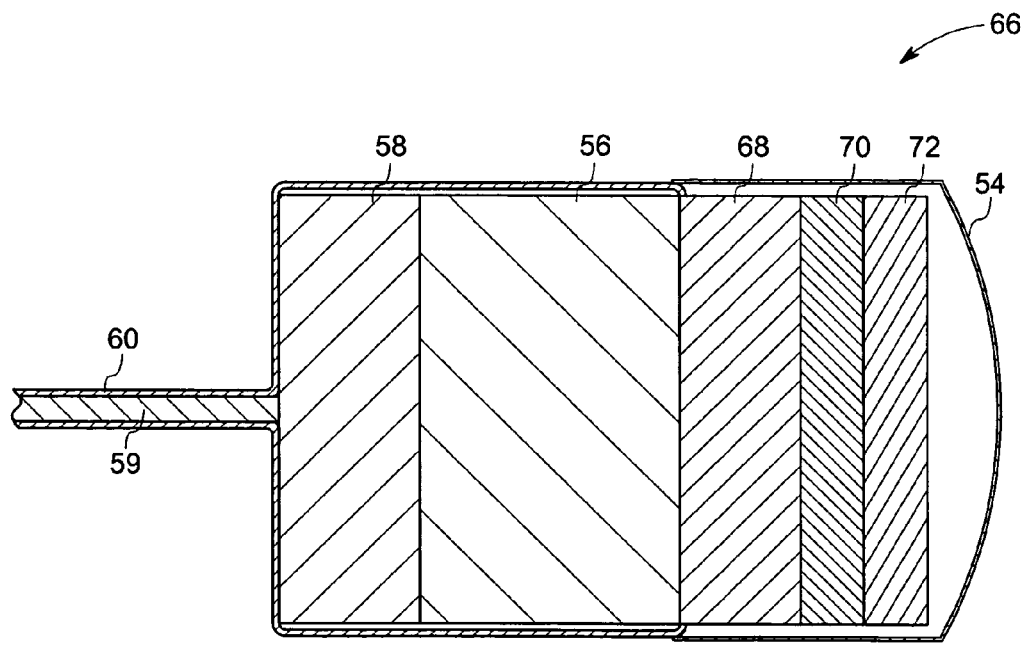
FIG. 3 is a cross-sectional side view of a cut away of the transducer assembly of FIG. 2 along cross-sectional line 3—3.

FIG. 3 illustrates a cross-sectional side view 66 of a cut away of the transducer assembly 52 of FIG. 2 along cross-sectional line 3—3. As illustrated in FIG. 3, the cross-sectional side view 66 of the transducer assembly 52 of FIG. 2 includes the backing layer 56. Furthermore, the transducer assembly also includes the support plate 58. The array of transducer elements 68 is disposed adjacent to the front face of the backing layer 56. In addition, a first matching layer 70, having a first front face and a first rear face, may be positioned adjacent to the front face of the array of transducer elements 68. Also, as illustrated in FIG. 3, a second matching layer 72, having a second front face and a second rear face may be disposed adjacent to the first front face of the first matching layer 70. Furthermore, the lens 54 may be disposed adjacent to the front face of the second matching layer 72. As will be appreciated by one skilled in the art, the lens 54 may include a portion configured to cover the array of transducer elements 68 and the matching layers 70, 72, as illustrated in FIG. 3.

Figure 4:
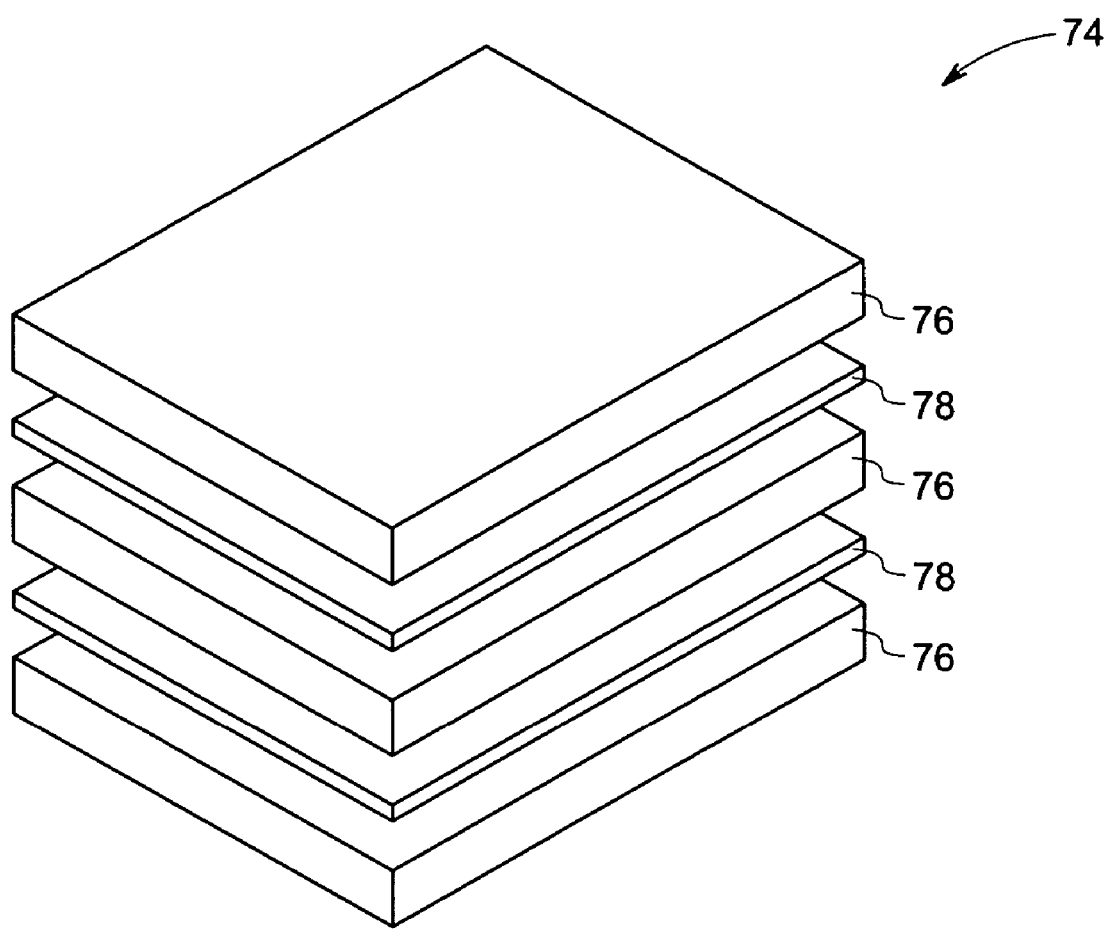
FIG. 4 is a perspective view illustrating an exemplary embodiment of a stacked composite structure of backing material with enhanced thermal conductivity for use in a transducer assembly according to aspects of the present technique.

As mentioned hereinabove, the transducer assembly 52 (see FIG. 2) includes a backing layer 56. FIG. 4 illustrates an exemplary composite structure 74 of the backing layer 56 that facilitates the dissipation of the heat that may be trapped in the central region of the transducer assembly 52. The central region may include the array of transducer elements 68, the first matching layer 70, the second matching layer 72 and the lens 54 (see FIG. 3). By implementing the backing layer 56 having a composite structure 74, the acoustic performance of the transducer assembly 52 may be advantageously enhanced. In accordance with an embodiment of the present technique, the heat that may be trapped in a central region of the transducer assembly 52 may be dissipated via the composite structure 74 that is coupled to the rear face of the array of transducer elements 68. For example, the heat from the central region of the transducer assembly 52 may be dissipated to a plurality of sides and/or a rear side of the composite structure 74. As will be appreciated by one skilled in the art, the backing layer 56 is fabricated employing materials that exhibit desirable acoustic properties. For example, the backing layer 56 may be fabricated employing material, such as, but not limited to, a composite of epoxy, tungsten particles and small silicone spheres. However, such materials typically exhibit low thermal conductivity. For example the thermal conductivity of the backing material varies in a range of about 0.2 Watts/meter/Kelvin (W/m/K) to about 0.4 W/m/K. Hence, altering the properties of the backing layer 56 to enhance the thermal conductivity may disadvantageously lead to deterioration of the performance of the transducer assembly 52.

Figure 5:
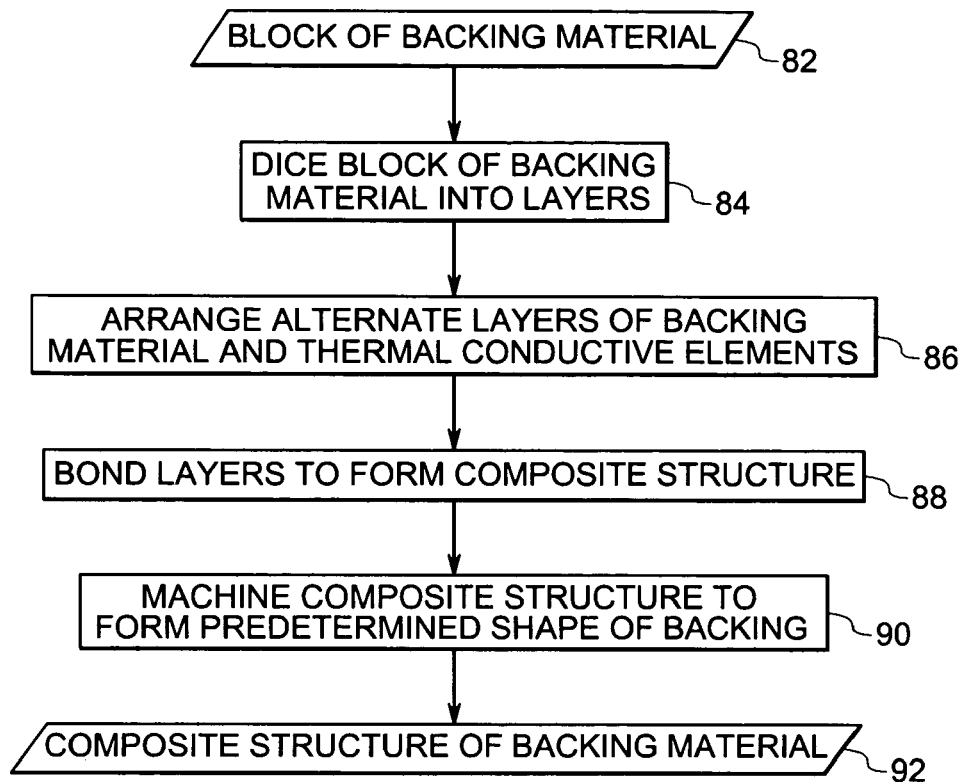
FIG. 5 is a flow chart depicting steps for forming a composite structure of backing material according to aspects of the present technique.
Figure 6:
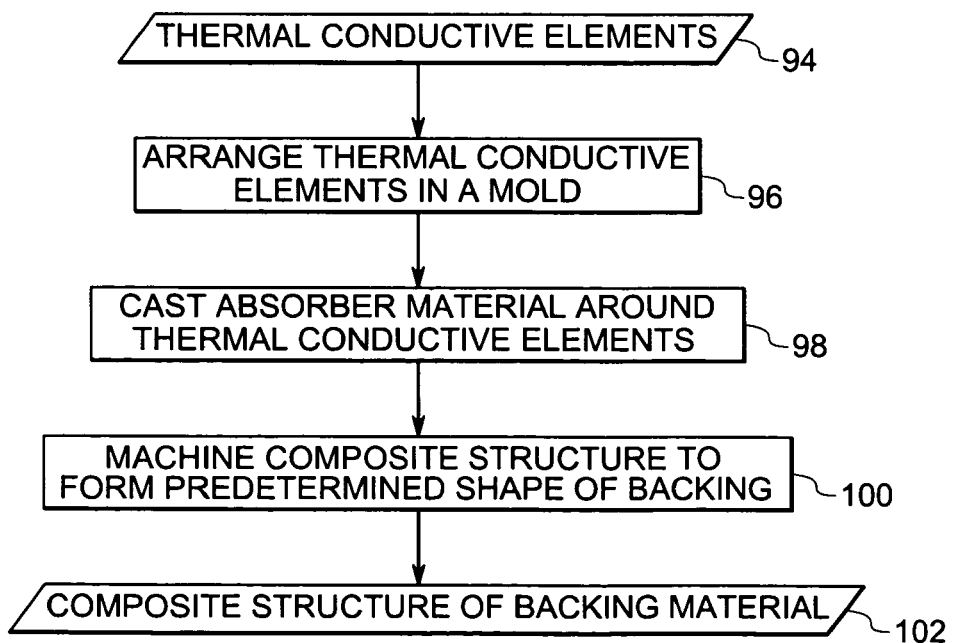
FIG. 6 is a flow chart depicting steps of an alternate method for forming a composite structure according to further aspects of the present technique.

According to one aspect of the present technique, the thermal conductivity of the backing layer 56 may be advantageously enhanced by introducing a material possessing high thermal conductivity to form a composite structure 74 of backing material while maintaining the acoustic properties of the backing layer 56. FIGS. 4–6 illustrate an exemplary structure and methods for forming the composite structure 74 of the backing layer 56 of FIG. 2, according to exemplary embodiments of the present technique. In a presently contemplated configuration, the composite structure 74 of backing material includes alternating layers of backing material and thermally conductive elements. FIG. 4 is a diagrammatical view of an embodiment of the stacked composite structure 74 of backing material. The composite structure 74 includes a arrangement wherein layers of backing material 76 are alternatively stacked with layers of material possessing high thermal conductivity 78 (hereinafter referred to as thermal conductive elements 78).

In accordance with an exemplary embodiment of the present technique, a flow chart illustrating a method for forming the composite structure 74 of backing material of FIG. 4 is provided with reference to FIG. 5. As illustrated in FIG. 5, a block of backing material, as depicted in block 82, may be employed to form the composite structure 74 of backing material with enhanced thermal conductivity. The method for forming the composite structure 74 begins at step 84, where the block of backing material 82 is diced to form a plurality of backing material layers 76 (see FIG. 4). The thickness of the backing material layers 76 may vary in a range from about 0.2 mm to about 2.0 mm.

At step 86, the backing material layers 76 are stacked in an arrangement, wherein the backing material layers 76 are alternatively stacked with layers of material of high thermal conductivity 78 (thermal conductive elements 78). The thermal conductive elements 78 may include a metal foil, wherein the metal foil may include, for example, a copper foil, an aluminum foil, and alloys or combinations thereof. However, on the other hand, the thermal conductive elements may include highly conductive non-metals, such as, but not limited to, a pyrolytic graphite or a boron nitride. The thickness of the thermal conductive elements 78, such as the metal foil, may vary in a range from about 0.01 mm to about 0.04 mm. Once stacked, the pitch between the thermal conductive elements 78 may vary in a range from about 0.2 mm to about 2.0 mm. Alternatively, the thermal conductive elements 78 may comprise a material with high thermal conductivity in the form of wires, rods, flexible circuit traces, flexible circuit ground planes, and combinations thereof. In a presently contemplated configuration of the present technique, in order to achieve an acoustically uniform attenuating medium, it may be advantageous to limit the thickness of the thermal conductive elements 78 to be significantly lower than a wavelength of sound at an operating frequency of the transducer assembly 52. In addition, the number of thermal conductive elements 78 that may be included in the composite structure 74 may be chosen such that the thermal conductivity of the composite structure 74 is advantageously enhanced while having negligible effect on the acoustic properties of the composite structure 74.

Additionally, in accordance with an exemplary embodiment of the present technique, the pitch between the thermal conductive elements 78 may be varied with respect to one another based upon a location in the transducer assembly 52. As will be appreciated by one skilled in the art, the central region of the transducer assembly 52 is a heat-generating region. Hence, a higher density of thermal conductive elements 78 may be disposed in the central region of the transducer assembly 52, while a lower density of thermal conductive elements 78 may be disposed in a peripheral region of the transducer assembly 52, thereby resulting in reduced fabrication cost.

Furthermore, as illustrated in FIG. 2, the ground plane 62 may be split to provide increased isolation between a transmitting region and a receiving region of the transducer assembly 52. According to an exemplary embodiment of the present technique, separate sets of thermal conductive elements 78 may be employed for the transmitting and receiving regions of the transducer assembly 52, thereby resulting in the reduction of noise and crosstalk levels.

As previously discussed, it may be desirable to enhance the thermal conductivity of the backing material by introducing a material of high thermal conductivity while maintaining the acoustic properties of the backing material. In a presently contemplated configuration, a total volume of the thermal conductive elements 78 may be less than approximately 5 volume percent of a volume of the backing material. Further, it may be advantageous to limit the total volume of the thermal conductive elements 78 to less than approximately 3 volume percent of the volume of the backing material.

In addition, it may be advantageous to directionally align the thermal conductive elements 78 with the backing material layers 76 to facilitate the efficient dissipation of heat from the transducer assembly 52. For example, the thermal conductive elements 78 may be disposed in a direction parallel to the direction of the backing material layers 76 to advantageously enhance the thermal conductivity of the composite structure 74. Furthermore, in accordance with an exemplary embodiment of the present technique, the thermal conductive elements 78 may be disposed in the composite structure 74 such that they extend through the composite structure from the heat-generating region of the transducer assembly 52 to heat sinks (not shown) or other thermal conductive elements 78 that may be positioned on a periphery of the composite structure 74. As will be appreciated by one skilled in the art, the heat-generating region of the transducer assembly 52 may include the transducer elements 68, the matching layers 70, 72 and the lens 54 (see FIG. 3). Additionally, the thermal conductive elements may be distributed throughout the composite structure 74 to facilitate minimizing any thermal resistance that may be present between a heat source point and a heat sink.

Returning to FIG. 5, at step 88, the stacked alternating layers of backing material 76 and thermal conductive elements 78 may be bonded to form the composite structure 74 of backing material. Furthermore, at step 90, the composite structure may be machined to form a predetermined shape of backing material to yield a composite structure 74 of backing material as depicted in block 92. For example, the composite structure may be machined to form a rectangular block having one face approximately equivalent to the size of the transducer array 68 (see FIG. 3).

According to an alternate embodiment of the present technique, thermal conductive elements 78 may be directly deposited onto the backing material layers 76. The backing material layers 76 may be subsequently bonded together to form the composite structure 74 of backing material.

FIG. 6 is a flow chart depicting an alternate method of forming the composite structure 74 of backing material, according to further aspects of the present technique. As suggested by the method summarized in FIG. 6, the thermal conductive elements 78, depicted in block 94, may be employed to form the composite structure 74 of backing material with enhanced thermal conductivity. Given the thermal conductive elements 78, the method for forming the composite structure begins at step 96, where the thermal conductive elements 78 may be arranged in a spaced relationship, wherein the spaced relationship may include a predetermined pattern. For example, the predetermined pattern may include parallel sheets of the thermal conductive elements positioned at a uniform pitch. Alternatively, the predetermined pattern may include a two dimensional (2D) array of thermal conductive elements 78, such as rods and strips, placed at a uniform pitch. Furthermore, the thermal conductive elements 78 that have been arranged in a spaced relationship may be disposed in a mold. At step 98, the backing material may be cast around the thermal conductive elements 78 to form the composite structure 74 of backing material. In addition, at step 100, the composite structure may be machined to form a predetermined shape of backing material to yield a composite structure 74 of backing material as depicted in block 102. As previously described the composite structure may be machined to form a rectangular block having one face approximately equivalent to the size of the transducer array 68 (see FIG. 3).

The composite structure 74 of backing material formed employing methods described hereinabove may be employed in an ultrasound system as illustrated in FIG. 1.

As mentioned hereinabove, the plurality of thermal conductive elements 78 that may be included in the composite structure 74 of backing material facilitate the transfer of heat from the center of the transducer assembly to a plurality of points on the composite structure 74 of backing material. For example, the points of heat dissipation on the composite structure 74 of backing material may include one or more sides of the composite structure 74. Additionally, the points of heat dissipation may include a rear side of the composite structure 74.

Furthermore, in accordance with an exemplary embodiment of the present technique, a thermal conductive structure, such as the central plate 59 (see FIG. 2), configured to provide a thermal path for the transfer of heat away from the plurality of points on the composite structure 74 of backing material of the transducer assembly 52, is presented. For example, the thermal conductive structure 59 may be employed to provide a thermal path to transfer the heat away from the heat-generating region of the transducer assembly 52 via the composite structure 74 toward a rear region of a probe. The heat may then be dissipated into the surrounding air, thereby facilitating the reduction of temperature of the patient contact area. Alternatively, an active cooling mechanism may be employed to transfer the heat away from the heat-generating region of the transducer assembly 52 via the composite structure 74 of backing material. For example, the active cooling mechanism may include a heat transducer cooling arrangement that facilitates the removal of heat employing coolants.

The composite structure 74 of backing material described hereinabove, advantageously enables the efficient dissipation of heat from the heat-generating region of the transducer assembly 52. The thermal conductivity of the backing material that is in direct contact with the heat-generating region may be advantageously enhanced by the introduction of thermal conductive elements 78 that facilitate the transfer of heat from the heat-generating region to other regions of the transducer assembly.

Thus the effective dissipation of heat from the transducer assembly enables the reduction of ultrasound face temperature thereby allowing the probe to be operated at a higher transmit power yielding significant improvements in diagnostic imaging. Furthermore, the methods for forming the composite structure 74 of backing material minimize changes to the acoustic properties of the backing material thereby enhancing the performance of the transducer assembly 52.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A composite structure of a backing material for use in a transducer, the composite structure comprising:
   a plurality of layers of backing material alternatingly arranged between a plurality of thermal conductive elements, wherein the plurality of thermal conductive elements are configured to transfer heat from a center of the transducer to a plurality of points on the composite structure of backing material, and wherein a volume of the thermal conductive elements comprises up to about 5 volume percent of a volume of the backing material.

2. The composite structure of claim 1, wherein the plurality of layers of backing material and the plurality of thermal conductive elements are bonded to form the composite structure.

3. The composite structure of claim 1, wherein the plurality of thermal conductive elements is disposed parallel to the plurality of layers of backing material.

4. The composite structure of claim 1, wherein the plurality of points on the composite structure of backing material comprises one or more sides of the composite structure of backing material.

5. The composite structure of claim 1, wherein the plurality of points on the composite structure of backing material comprises a rear side of the composite structure of backing material.

6. The composite structure of claim 1, wherein the backing material comprises an epoxy material.

7. The composite structure of claim 1, wherein a thickness of each of the plurality of layers of backing material is in a range from about 0.2 mm to about 2.0 mm.

8. The composite structure of claim 1, wherein the plurality of thermal conductive elements comprises a metal foil.

9. The composite structure of claim 8, wherein the metal foil is selected from the group consisting of a copper foil, an aluminum foil, and alloys or combinations thereof.

10. The composite structure of claim 1, wherein the plurality of thermal conductive elements comprises a conductive non-metal.

11. The composite structure of claim 10, wherein the conductive non-metal comprises at least one of a pyrolytic graphite and a boron nitride.

12. The composite structure of claim 1, wherein the plurality of thermal conductive elements is selected from the group consisting of wires, rods, flexible circuit traces, and combinations thereof.

13. The composite structure of claim 1, wherein a thickness of the plurality of thermal conductive elements is in a range from about 0.01 mm to about 0.04 mm.

14. The composite structure of claim 1, wherein a pitch between thermal conductive elements in the composite structure is in a range of about 0.2 mm to about 2.0 mm.

15. The composite structure of claim 1, wherein the plurality of thermal conductive elements is more dense at a central area of the transducer than at a peripheral area of the transducer.

16. A transducer assembly comprising:
a plurality of transducer elements disposed in a first layer having a first front face and a first rear face; and
an absorber disposed in a second layer having a second front face and a second rear face, wherein the absorber is disposed adjacent to the first rear face and is acoustically coupled to the first rear face, and wherein the absorber comprises a composite structure of backing material having thermal conductive elements dispersed therethrough, and wherein a volume of the thermal conductive elements comprises up to about 5 volume percent of a volume of the backing material.

17. The assembly of claim 16, further comprising a thermal conductive structure coupled to the composite structure of backing material, wherein the thermal conductive structure is configured to provide a thermal path from the composite structure of backing material to a heat dissipating structure.

18. The assembly of claim 17, wherein the thermal conductive structure comprises a metal sheet extending from a plurality of sides of the composite structure to an inside surface of a probe handle.

19. The assembly of claim 18, wherein the metal sheet comprises a copper sheet.

20. The assembly of claim 17, wherein the thermal conductive structure comprises a cooling system, wherein the cooling system is configured to transfer heat from the composite structure to a heat dissipating structure via a transducer cable.

21. The assembly of claim 16, wherein the composite structure of backing material comprises a plurality of layers of backing material alternatingly arranged between a plurality of thermal conductive elements, wherein the plurality of thermal conductive elements are configured to transfer heat from a center of the transducer to a plurality of points on the composite structure of backing material.

22. The assembly of claim 21, wherein the plurality of layers of backing material and the plurality of thermal conductive elements are bonded to form the composite structure.

23. The assembly of claim 21, wherein the plurality of thermal conducting elements is disposed parallel to the plurality of layers of backing material.

24. The assembly of claim 21, wherein the plurality of points on the composite structure of backing material comprises one or more sides of the composite structure of backing material.

25. The assembly of claim 21, wherein the plurality of points on the composite structure of backing material comprises a rear side of the composite structure of backing material.

26. The assembly of claim 21, wherein the backing material comprises an epoxy material.

27. The assembly of claim 26, wherein a thickness of each of the plurality of layers of backing material is in a range from about 0.2 mm to about 2.0 mm.

28. The assembly of claim 21, wherein the plurality of thermal conductive elements comprises a metal foil.

29. The assembly of claim 28, wherein the metal foil is selected from the group consisting of a copper foil, an aluminum foil, and alloys or combinations thereof.

30. The assembly of claim 21, wherein the plurality of thermal conductive elements comprises a conductive non-metal.

31. The assembly of claim 30, wherein the conductive non-metal comprises at least one of a pyrolytic graphite and a boron nitride.

32. The assembly of claim 21, wherein the plurality of thermal conductive elements is selected from the group consisting of wires, rods, flexible circuit traces, and combinations thereof.

33. The assembly of claim 21, wherein a pitch between thermal conductive elements in the composite structure is in a range of about 0.2 mm to about 2.0 mm.

34. The assembly of claim 21, wherein the plurality of thermal conductive elements is more dense at a central area of the transducer than at a peripheral area of the transducer.

35. The assembly of claim 21, wherein a thickness of the plurality of thermal conductive elements is in a range from about 0.01 mm to about 0.04 mm.

36. The assembly of claim 16, comprising a metal foil that is configured to provide electrical shielding to the plurality of transducer elements.

37. An ultrasound system, the system comprising:
an acquisition subsystem configured to acquire ultrasound data, wherein the acquisition subsystem comprises at least one transducer assembly, wherein the transducer assembly comprises a composite structure of backing material having thermal conductive elements dispersed therethrough, and wherein a volume of the thermal conductive elements comprises up to about 5 volume percent of a volume of the backing material; and
a processing subsystem configured to process the ultrasound data acquired via the acquisition subsystem.

38. The ultrasound system of claim 37, wherein the acquisition subsystem comprises at least one transducer assembly configured to facilitate the acquisition of the ultrasound data.

39. The ultrasound system of claim 38, wherein the at least one transducer assembly comprises a plurality of transducer elements disposed in a first layer having a first front face and a first rear face, an absorber disposed in a second layer having a second front face and a second rear face, wherein the absorber is disposed adjacent to the first rear face, and wherein the absorber comprises a composite structure of backing material having conductive elements dispersed therethrough.

40. The ultrasound system of claim 39, further comprising a disposing a thermal conductive structure, wherein the thermal conductive structure is configured to provide a thermal path from the composite structure of backing material to a heat dissipating structure.

41. The ultrasound system of claim 40, wherein the thermal conductive structure comprises a metal sheet extending from a plurality of sides of the composite structure to an inside surface of a probe handle.

42. The ultrasound system of claim 41, wherein the metal sheet comprises a copper sheet.

43. The ultrasound system of claim 40, wherein the thermal conductive structure comprises a cooling system, wherein the cooling system is configured to transfer heat from the composite structure to a heat dissipating structure via a transducer cable.

44. The ultrasound system of claim 39, wherein the absorber comprises a plurality of layers of backing material alternatingly arranged between a plurality of thermal conductive elements, wherein the plurality of thermal conductive elements are configured to transfer heat from a center of the transducer to a plurality of points on the composite structure of backing material.

45. The ultrasound system of claim 44, wherein the plurality of layers of backing material and the plurality of thermal conductive elements are bonded to form the composite structure.

46. The ultrasound system of claim 44, wherein the plurality of thermal conducting elements is disposed parallel to the plurality of layers of backing material.

47. The ultrasound system of claim 44, wherein the plurality of points on the composite structure of backing material comprises one or more sides of the composite structure of backing material.

48. The ultrasound system of claim 44, wherein the plurality of points on the composite structure of backing material comprises a rear side of the composite structure of backing material.

49. The ultrasound system of claim 44, wherein the backing material comprises an epoxy material.

50. The ultrasound system of claim 44, wherein a thickness of each of the plurality of layers of backing material is in a range from about 0.2 mm to about 2.0 mm.

51. The ultrasound system of claim 44, wherein the plurality of thermal conductive elements comprises a metal foil.

52. The ultrasound system of claim 51, wherein the metal foil is selected from the group consisting of a copper foil, an aluminum foil, and alloys or combinations thereof.

53. The ultrasound system of claim 44, wherein the plurality of thermal conductive elements comprises a conductive non-metal.

54. The ultrasound system of claim 53, wherein the conductive non-metal comprises at least one of a pyrolytic graphite and a boron nitride.

55. The ultrasound system of claim 44, wherein the plurality of thermal conductive elements is selected from the group consisting of wires, rods, flexible circuit traces, and combinations thereof.

56. The ultrasound system of claim 44, wherein a pitch between thermal conductive elements in the composite structure is in a range of about 0.2 mm to about 2.0 mm.

57. The ultrasound system of claim 44, wherein a thickness of the plurality of thermal conductive elements is in a range from about 0.01 mm to about 0.04 mm.

58. The ultrasound system of claim 44, wherein the plurality of thermal conductive elements is more dense at a central area of the transducer than at a peripheral area of the transducer.

59. The ultrasound system of claim 37, comprising a display module configured to display the processed ultrasound data.

60. The ultrasound system of claim 37, comprising a user interface configured to enable an operator to acquire and/or display the ultrasound data.

61. The ultrasound system of claim 37, comprising a data repository module configured to store the ultrasound data.

62. The ultrasound system of claim 37, comprising an imaging workstation module configured to manipulate the ultrasound data.

63. A composite structure of a backing material for use in a transducer, the composite structure comprising:
a plurality of layers of backing material alternatingly arranged between a plurality of thermal conductive elements, wherein the plurality of thermal conductive elements are configured to transfer heat from a center of the transducer to a plurality of points on the composite structure of backing material, and wherein the plurality of thermal conductive elements is more dense at a central area of the transducer than at a peripheral area of the transducer.

64. The composite structure of claim 63, wherein the plurality of layers of backing material and the plurality of thermal conductive elements are bonded to form the composite structure.

65. The composite structure of claim 63, wherein the plurality of thermal conductive elements is disposed parallel to the plurality of layers of backing material.

66. The composite structure of claim 63, wherein the plurality of points on the composite structure of backing material comprises one or more sides of the composite structure of backing material.

67. The composite structure of claim 63, wherein the plurality of points on the composite structure of backing material comprises a rear side of the composite structure of backing material.

68. The composite structure of claim 63, wherein the backing material comprises an epoxy material.

69. The composite structure of claim 63, wherein a thickness of each of the plurality of layers of backing material is in a range from about 0.2 mm to about 2.0 mm.

70. The composite structure of claim 63, wherein the plurality of thermal conductive elements comprises a metal foil.

71. The composite structure of claim 70, wherein the metal foil is selected from the group consisting of a copper foil, an aluminum foil, and alloys or combinations thereof.

72. The composite structure of claim 63, wherein the plurality of thermal conductive elements comprises a conductive non-metal.

73. The composite structure of claim 72, wherein the conductive non-metal comprises at least one of a pyrolytic graphite and a boron nitride.

74. The composite structure of claim 63, wherein the plurality of thermal conductive elements is selected from the group consisting of wires, rods, flexible circuit traces, and combinations thereof.

75. The composite structure of claim 63, wherein a thickness of the plurality of thermal conductive elements is in a range from about 0.01 mm to about 0.04 mm.

76. The composite structure of claim 63, wherein a pitch between thermal conductive elements in the composite structure is in a range of about 0.2 mm to about 2.0 mm.

77. A transducer assembly comprising:
a plurality of transducer elements disposed in a first layer having a first front face and a first rear face; and
an absorber disposed in a second layer having a second front face and a second rear face, wherein the absorber is disposed adjacent to the first rear face and is acoustically coupled to the first rear face, wherein the absorber comprises a composite structure of backing material having thermal conductive elements dispersed therethrough, and wherein the plurality of thermal conductive elements is more dense at a central area of the transducer than at a peripheral area of the transducer.

78. The assembly of claim 77, further comprising a thermal conductive structure coupled to the composite structure of backing material, wherein the thermal conductive structure is configured to provide a thermal path from the composite structure of backing material to a heat dissipating structure.

79. The assembly of claim 78, wherein the thermal conductive structure comprises a metal sheet extending from a plurality of sides of the composite structure to an inside surface of a probe handle.

80. The assembly of claim 79, wherein the metal sheet comprises a copper sheet.

81. The assembly of claim 78, wherein the thermal conductive structure comprises a cooling system, wherein the cooling system is configured to transfer heat from the composite structure to a heat dissipating structure via a transducer cable.

82. The assembly of claim 77, wherein the composite structure of backing material comprises a plurality of layers of backing material alternatingly arranged between a plurality of thermal conductive elements, wherein the plurality of thermal conductive elements are configured to transfer heat from a center of the transducer to a plurality of points on the composite structure of backing material.

83. The assembly of claim 82, wherein the plurality of layers of backing material and the plurality of thermal conductive elements are bonded to form the composite structure.

84. The assembly of claim 82, wherein the plurality of thermal conducting elements is disposed parallel to the plurality of layers of backing material.

85. An ultrasound system, the system comprising:
an acquisition subsystem configured to acquire ultrasound data, wherein the acquisition subsystem comprises at least one transducer assembly, wherein the transducer assembly comprises a composite structure of backing material having thermal conductive elements dispersed therethrough, and wherein the plurality of thermal conductive elements is more dense at a central area of the transducer than at a peripheral area of the transducer; and
a processing subsystem configured to process the ultrasound data acquired via the acquisition subsystem.

86. The ultrasound system of claim 85, wherein the acquisition subsystem comprises at least one transducer assembly configured to facilitate the acquisition of the ultrasound data.

87. The ultrasound system of claim 86, wherein the at least one transducer assembly comprises a plurality of transducer elements disposed in a first layer having a first front face and a first rear face, an absorber disposed in a second layer having a second front face and a second rear face, wherein the absorber is disposed adjacent to the first rear face, and wherein the absorber comprises a composite structure of backing material having conductive elements dispersed therethrough.

88. The ultrasound system of claim 87, further comprising a disposing a thermal conductive structure, wherein the thermal conductive structure is configured to provide a thermal path from the composite structure of backing material to a heat dissipating structure.

89. The ultrasound system of claim 88, wherein the thermal conductive structure comprises a metal sheet extending from a plurality of sides of the composite structure to an inside surface of a probe handle.

90. The ultrasound system of claim 89, wherein the metal sheet comprises a copper sheet.

91. The ultrasound system of claim 88, wherein the thermal conductive structure comprises a cooling system, wherein the cooling system is configured to transfer heat from the composite structure to a heat dissipating structure via a transducer cable.

92. The ultrasound system of claim 87, wherein the absorber comprises a plurality of layers of backing material alternatingly arranged between a plurality of thermal conductive elements, wherein the plurality of thermal conductive elements are configured to transfer heat from a center of the transducer to a plurality of points on the composite structure of backing material.

93. The ultrasound system of claim 92, wherein the plurality of layers of backing material and the plurality of thermal conductive elements are bonded to form the composite structure.

94. The ultrasound system of claim 85, comprising a display module configured to display the processed ultrasound data.

95. The ultrasound system of claim 85, comprising a user interface configured to enable an operator to acquire and/or display the ultrasound data.

96. The ultrasound system of claim 85, comprising a data repository module configured to store the ultrasound data.

97. The ultrasound system of claim 85, comprising an imaging workstation module configured to manipulate the ultrasound data.

* * * * *